United States Patent
Kahler et al.

(10) Patent No.: US 10,595,883 B2
(45) Date of Patent: Mar. 24, 2020

(54) SURGICAL MOTOR

(71) Applicant: Aesculap AG, Tuttlingen (DE)

(72) Inventors: Thomas Kahler, Seitingen-Oberflacht (DE); Jürgen Barth, Denkingen (DE); Stephanie Auber, Tuttlingen (DE); Roland-Alois Högerle, Tuttlingen (DE)

(73) Assignee: Aesculap AG (DE)

( * ) Notice: Subject to any disclaimer, the term of this patent is extended or adjusted under 35 U.S.C. 154(b) by 197 days.

(21) Appl. No.: 15/546,581

(22) PCT Filed: Jan. 28, 2016

(86) PCT No.: PCT/EP2016/051809
§ 371 (c)(1),
(2) Date: Jul. 26, 2017

(87) PCT Pub. No.: WO2016/124478
PCT Pub. Date: Aug. 11, 2016

(65) Prior Publication Data
US 2018/0008289 A1  Jan. 11, 2018

(30) Foreign Application Priority Data

Feb. 2, 2015  (DE) .................. 10 2015 101 487

(51) Int. Cl.
*A61B 17/16* (2006.01)
*H02K 3/47* (2006.01)
*H02K 5/02* (2006.01)

(52) U.S. Cl.
CPC .......... *A61B 17/1628* (2013.01); *H02K 3/47* (2013.01); *H02K 5/02* (2013.01)

(58) Field of Classification Search
CPC .. H02K 3/47; H02K 3/18; H02K 3/28; H02K 15/12; H02K 1/24
(Continued)

(56) References Cited

U.S. PATENT DOCUMENTS

| 6,166,468 A * | 12/2000 | Suzuki | H02K 1/148 |
| | | | 310/216.061 |
| 2004/0113504 A1* | 6/2004 | Agnes | H02K 1/17 |
| | | | 310/154.08 |

(Continued)

FOREIGN PATENT DOCUMENTS

| CN | 101882847 A | 11/2010 |
| CN | 102449884 A | 5/2012 |

(Continued)

OTHER PUBLICATIONS

International Search Report and Written Opinion for International Application No. PCT/EP2016/051809, dated Apr. 5, 2016—10 Pages.

(Continued)

*Primary Examiner* — Nathaniel C Chukwurah
(74) *Attorney, Agent, or Firm* — RatnerPrestia

(57) ABSTRACT

A coil former for an electric motor, in particular a high-speed surgical motor, in which a rotor is surrounded concentrically by the substantially hollow-cylindrical coil former, carries at least one stator winding. To ensure that as narrow an air gap as possible is permanently maintained between the coil former, which is preferably produced using an injection-molding method often with complex shaping, and a rotor, which runs in the coil former, the coil former is formed either by a non-conductive fully ceramic body, or is in the form of a composite body in which at least one dimension-stabilizing frame element is embedded by injection-molding with plastic in a plastic body which is preferably produced by injection molding.

18 Claims, 4 Drawing Sheets

(58) Field of Classification Search
USPC .................................. 173/217, 213, 216
See application file for complete search history.

(56) References Cited

U.S. PATENT DOCUMENTS

| | | | |
|---|---|---|---|
| 2010/0261140 A1* | 10/2010 | Klee | H02K 5/128 |
| | | | 433/131 |
| 2012/0068557 A1* | 3/2012 | Duesing | H02K 5/08 |
| | | | 310/43 |
| 2012/0274167 A1 | 11/2012 | Kim | |
| 2013/0088115 A1 | 4/2013 | Sperandei | |
| 2013/0134809 A1 | 5/2013 | Phillips et al. | |
| 2014/0077648 A1 | 3/2014 | Bräuer et al. | |
| 2016/0126796 A1 | 5/2016 | Teimel et al. | |

FOREIGN PATENT DOCUMENTS

| | | |
|---|---|---|
| DE | 4438132 A1 | 5/1996 |
| DE | 102010049524 A1 | 4/2012 |
| EP | 2135567 A1 | 12/2009 |
| EP | 2597757 A1 | 5/2013 |
| JP | 2004180457 A | 6/2004 |
| JP | 2007236026 A | 9/2007 |
| JP | 2011101578 A | 5/2011 |
| WO | 2011113887 A2 | 9/2011 |

OTHER PUBLICATIONS

German Search Report for German Application No. 10 2015 101 487.4, dated Dec. 15, 2015—11 Pages.
Chinese Office Action for Chinese Application No. 201680008365.6, dated Dec. 11, 2018, with translation, 16 pages.
Chinese Office Action for Chinese Application No. 201680008365.6, dated Aug. 20, 2019, 10 pages.
Japanese Notification of Reasons for Rejection for Japanese Application No. 2017-540736, dated Jan. 21, 2020 with translation, 15 pages.

* cited by examiner

SURGICAL MOTOR

RELATED APPLICATIONS

This is the United States national phase entry of International Application No. PCT/EP2016/051809, filed Jan. 28, 2016, which is related to and claims the benefit of priority of German Application No. DE 10 2015 101 487.4, filed Feb. 2, 2015. The contents of International Application No. PCT/EP2016/051809 and German Application No. DE 10 2015 101 487.4 are incorporated by reference herein in their entireties.

FIELD

The invention relates to an electric motor, in particular a high-speed surgical motor, comprising a rotor which is surrounded concentrically by a substantially hollow-cylindrical coil former which carries at least one stator winding. Furthermore, the invention relates to a coil former to be used in such motor.

Motors of this type excel by the fact that they provide very high outputs with minimum construction so that rotational speeds up to 200,000 rpm can be easily reached. Such motors therefore are especially suited for driving surgical instruments.

BACKGROUND

A generic motor is described, for example, in the document EP 2 135 567 A1. In this known case, however, the structure is such that the stator winding is embedded in a cast compound.

Compared to this, modern motors include a coil former usually made from plastic material by injection molding to which at least one stator winding is applied. Said design enables the at least one stator winding to be accommodated in the motor in an even more space-saving manner. At the same time, the manufacturing costs can be reduced the coil former being injection-molded in a more and more complex shape which enables the coil former to be permanently fixed in the motor housing and the coil winding having a predetermined configuration to be permanently fixed without any additional components.

In order to further increase the output of said motors efforts are made to further reduce the air gaps between the rotor and the coil former, for example to ranges of from 0.1 to 0.3 mm, taking the further special feature into account that the coil formers frequently have a considerable axial length as compared to the inner diameter. It has turned out that in conventional motors of this constructional design sudden blocking of the rotor entailed early failure.

SUMMARY

An electric motor of the afore-described type is further developed so that, while maintaining simple assembly even when a relatively long stator winding is used, it is reliably ensured that the motor output remains constantly high throughout the entire service life of the motor. In accordance with the invention, it was found that the coil former usually manufactured by injection molding with relatively complex geometry, i.e. with different fit surfaces having narrow tolerances relative to each other in space, especially when having a relatively large axial length as compared to the diameter, is subjected to smallest uncontrolled deformations, by which the air gap becomes irregular over the length of the rotor, already upon applying the stator winding and, resp., in the successive mounting steps. In the course of the operation of the motor during which the latter is regularly prepared and, resp., is subjected to a sterilization process, for example to steam pressure sterilization, said irregularity within the air gap is continuously increased, until the rotor finally blocks.

In accordance with the invention, the coil former is formed either by a non-conductive fully ceramic body or is in the form of a composite body in which at least one dimension-stabilizing frame element is embedded by injection molding with plastic in a plastic body which is produced by injection molding. The use of a fully ceramic body is useful for simpler geometries so as to minimize the manufacturing costs. The configuration of the coil former as composite body offers the special advantage that the manufacturing costs may be continued to be minimized and the shaping of the coil former may be invariably complex. By the injection molding process according to the invention an especially intimate connection is made between the composite components so that the frame element imparts a considerably increased strength to the coil former even when it claims a very small volume only, whereby the afore-described uncontrolled deformations of the coil former do no longer occur even during long-term operation and even with repeated preparation of the electric motor. The toothing can be even improved by a specific surface treatment of the frame element. Thus, it is possible to work with minimum air gaps and, in this way, to provide a high motor output throughout the entire service life of the motor, namely even when the coil formers have a relatively large axial length.

It has turned out that already, when the frame element takes the simple shape of a sleeve body, sufficient additional strength is provided so as to provide the long-term functional reliability of the motor.

Preferably, the sleeve body is made of non-conductive material, wherein at least in portions it forms a cylindrical inner surface of the coil former. Said configuration safeguards the dimensional stability of the coil former at the decisive positions, i.e. where it is important to permanently maintain the air gap from the rotor.

During tests, it has turned out that for sufficient increase in the dimensional stability it is sufficient already, when the sleeve body is formed to have a wall thickness which is within the range of from $(0.01$ to $0.03) \times D$, with D being the inner diameter of the coil former. In this way, the overall construction of the coil former remains largely unaffected by the modification.

Surgical electric motors operate with rotors having an outer diameter of approx. 12 mm. In this case, the wall thickness of the sleeve body may range from 0.1 to 0.5 mm.

When the frame element is formed by a ceramic component, especially an oxide ceramic component, it may be directly adjacent to the rotor so that it need not be injection molded radially inwardly with plastic. Moreover, a surface which is well suited for toothing with the plastic material can be imparted to the ceramic component by simple method steps. The inner diameter of the ceramic sleeve may be machined, with reasonable expenditure, to the respective exact dimension so as to realize even minimum air gaps. Ceramic materials of this type moreover offer the advantage of being adapted to be easily sterilized by superheated steam.

BRIEF DESCRIPTION OF THE DRAWING FIGURES

Hereinafter, by way of schematic drawings an embodiment of the invention is illustrated in detail, wherein.

DETAILED DESCRIPTION

Figure 5:
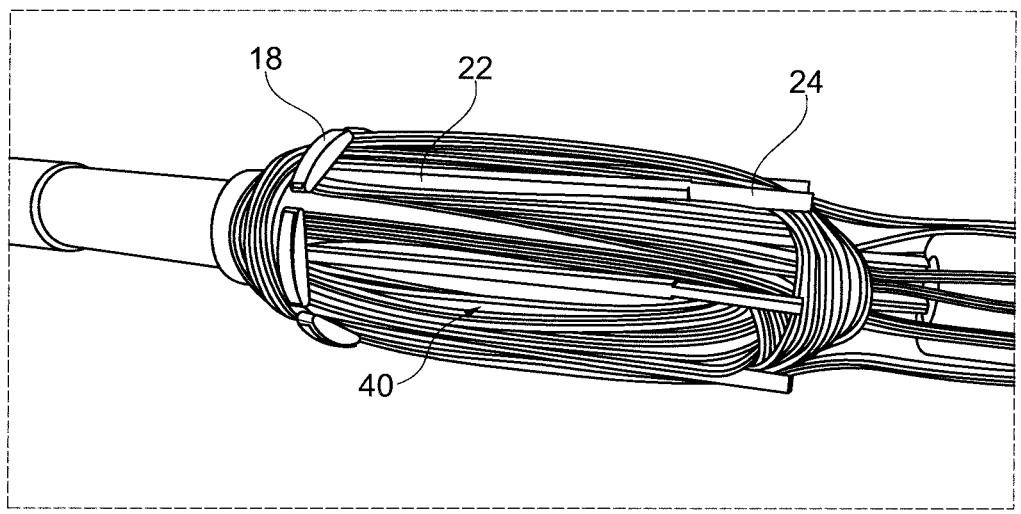
FIG. 5 shows a perspective view of the stator winding applied to the coil former.

In the Figures, the reference numeral 10 denotes the coil former of an electric motor not shown in detail which can be a high-speed surgical motor, for example. The substantially hollow-cylindrically designed coil former 10 which carries at least one stator winding 40—as shown in FIG. 5—surrounds a rotor—not shown in detail—which usually carries a cylindrical permanent magnet. The rotor thus is surrounded concentrically by the substantially hollow-cylindrical coil former 10, wherein a continuous air gap is maintained which is within the tenth of mm range so as to minimize output losses of the motor.

Motors of this type have a small overall size. For example, the diameter of the rotor amounts to approx. 12 mm, the length L10 of the coil former being within the range of approx. 40 mm.

Since, apart from the fixation of the stator winding—as evident from FIG. 5—, further functions such as e.g. the stabilization in the motor housing are conferred upon the coil former for minimizing the overall size of the motor, a relatively complex shape is imparted to the coil former 10—as shown in FIGS. 1 to 5—so that it is usually designed as a precision plastic injection molded part. Accordingly, all known types of plastic which are suited for this kind of manufacture may be used. Examples of such plastic materials preferably are thermoplastics resistant to high temperature such as polyetheretherketone (PEEK) from the material group of the polyaryletherketones or polyphenylene sulfide (PPS).

The coil former 10 of the shown embodiment substantially takes the shape of a stepped cylindrical sleeve, comprising a first longer sleeve portion 12 and a second shorter sleeve portion 14. Between the two sleeve portions 12, 14 a fixing portion 16 is located at which six mushroom-shaped spoke members 18 evenly spread over the periphery are arranged. The lands denoted with 20 are continued on the side of the longer sleeve portion 12 in ribs 22 which run out in rib extensions 24 radially slightly tapered toward the front end (cf. FIG. 3). The longer sleeve portion 12 is formed to be thin-walled between the ribs 22.

It is evident from FIG. 5 that the spoke members 18, the ribs 22 and the rib extensions 24 assume the function of fixing the stator winding in an exactly structured form.

The shorter sleeve portion 14 is formed to be hollow-cylindrical having an outer diameter of about 11 mm.

Due to the small dimensions of the motor, it is resulting that the coil former 10 is a component to be manufactured in a highly precise manner in which minimum dimensions such as a spoke width B20 of 1 mm, a rib thickness S22 of 1.5 mm have to be exactly observed with tolerance widths of 0.05 mm. For reasons of economic efficiency, the coil former is in the form of a plastic injection molded part.

In order to be capable of further increasing the output of the motor it is important that the constructed space available is exploited as completely as possible for accommodating the stator winding—as shown in FIG. 5. In order to simultaneously guarantee the long-term stability of the motor the coil former 10 illustrated in the Figures excels by the fact that it is in the form of a composite body in which at least one dimension-stabilizing frame element is embedded by injection molding with plastic in the plastic body manufactured by injection molding which is emphasized in FIGS. 3 and 4 by cross hatching. In the shown embodiment, two ceramic sleeves 30, 32 of different diameter are concerned which extend over the entire length of the shorter sleeve portion 14 and over almost the entire length of the longer sleeve portion 12 and each of which ends in the area of the fixing portion 16.

Figure 1:
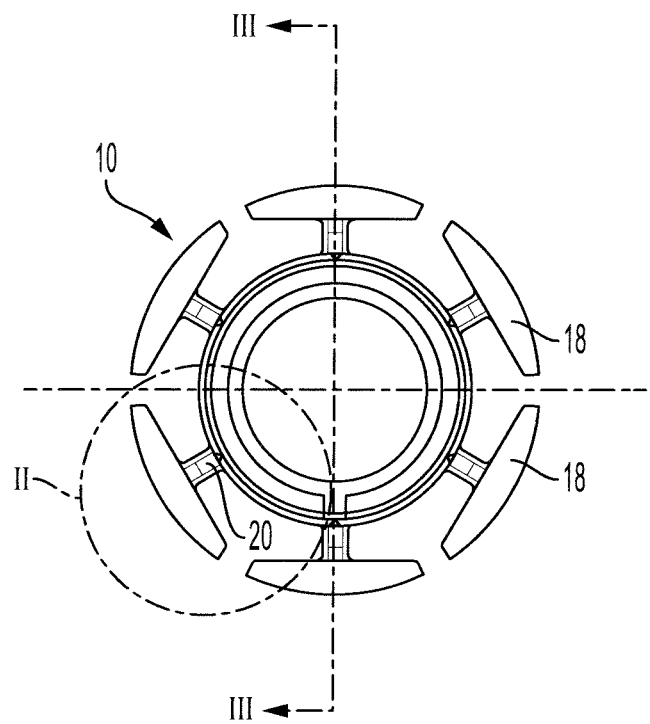
FIG. 1 shows a front view of a coil former for receiving a stator winding of a surgical electric motor.
Figure 2:
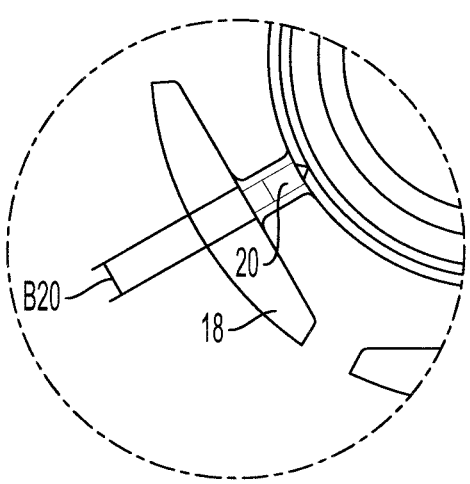
FIG. 2 shows an enlarged representation of the detail "II" in FIG. 1.
Figure 3:
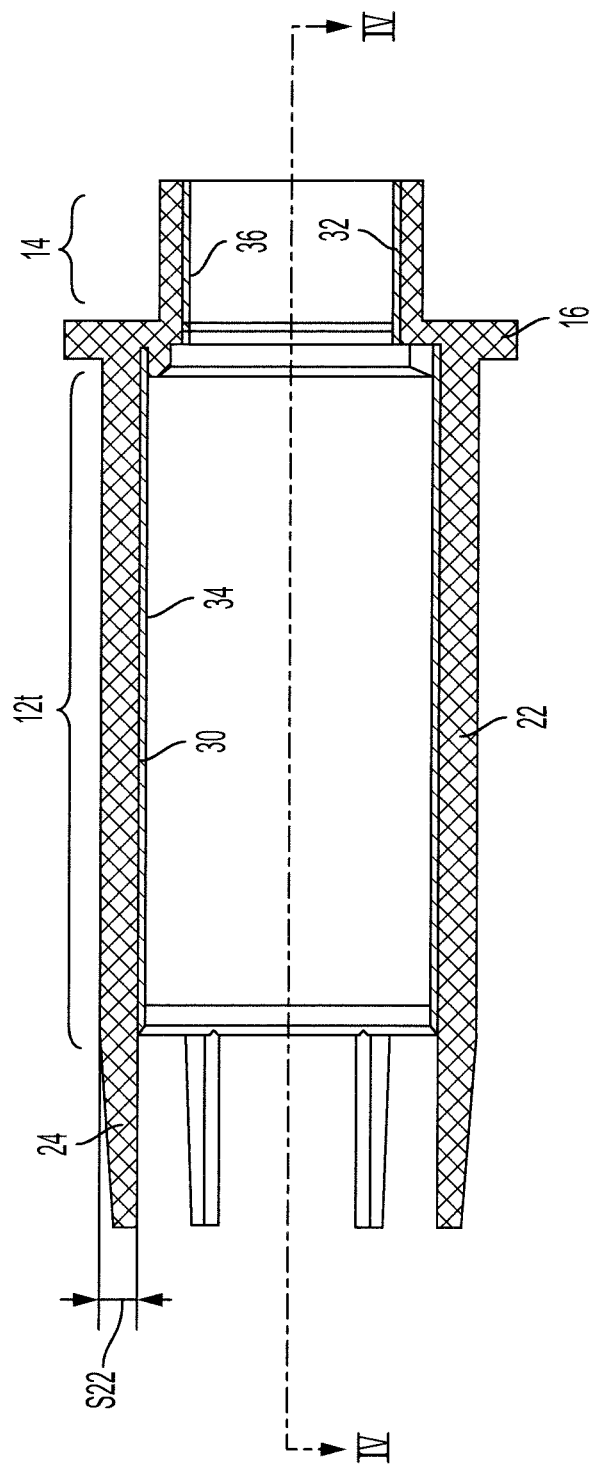
FIG. 3 shows the sectional view "III-III" according to FIG. 1.
Figure 4:
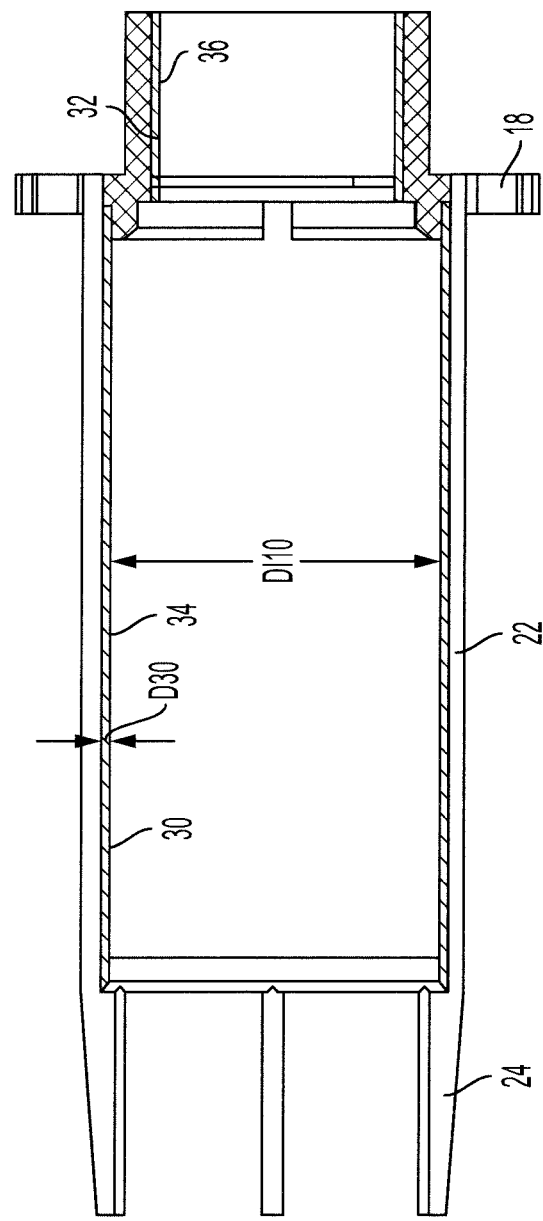
FIG. 4 shows the sectional view "IV-IV" in FIG. 3.

In the illustrated case, a ceramic component is chosen as a dimension-stabilizing frame element, because the frame element—as is evident from FIGS. 3 and 4—over large distances forms the inner surface 34, 36 of the coil former 10 which is opposed to the rotor and therefore is intended to be made from an electrically non-conductive material. Here especially oxide ceramics are appropriate. The inner surface 34, 36 of the frame element is ground to size for providing an as high dimensional accuracy as possible, which allows operating over the entire length of the stator with constant most narrow air gaps between the rotor and the stator. However, when the frame element is completely injection-molded with plastic, also other materials increasing the dimensional stability of the injection-molded body such as metallic materials or other ceramic materials, such as e.g. silicon carbide (SiC) or cermet materials, can be used.

In the shown embodiment, the share of plastic material in the coil former 10 is reduced as far as possible in that between the ribs 22 of the longer sleeve portion 12 no more plastic is provided, which is evident from the sectional representation according to FIG. 4. Nevertheless, it is possible to impart sufficiently high long-term dimensional stability to the coil former 10, even if the wall thickness D30 of the ceramic sleeve 30 is within the range of (0.01 to 0.03)×DI10, with DI10 being the inner diameter of the coil former 10. In the case of dimensioning according to the shown embodiment, the wall thickness D30 of the ceramic sleeve 30 and, resp., 32 ranges from 0.1 to 0.5 mm.

It has turned out that the described structure enables the coil former 10 to be equipped with a long-term dimensional stability not achieved so far while maintaining the conventional mounting steps for arranging the stator winding and for fixing in the motor housing, the long-term dimensional stability also withstanding repeated sterilizations and preparations of the motor, which allows to further reduce the air gap between the coil former and the rotor.

As a matter of course, deviations from the shown embodiment are possible without deviating from the basic idea of the invention. In the described case, the coil former is designed in a very complex manner with a plurality of fitting and functional surfaces so that, for reasons of the economic efficiency of manufacture, an injection-molded plastic body is used as a basis. In the case of simpler geometric shapes of the coil former it is also possible, however, to design the coil former completely in the form of a non-conductive fully ceramic body, which is considered to be an independent invention.

The dimension-stabilizing frame element may also take any other shape, as a matter of course, as long as it fulfills the function of increasing the dimensional stability. The frame element may as well include a network or grid structure.

Thus, the invention provides a coil former for an electric motor, in particular a high-speed surgical motor, in which a rotor is surrounded concentrically by the substantially hollow-cylindrical coil former which carries at least one stator winding. In order to ensure with reasonable effort, when applying the stator winding and during the further mounting steps, that as narrow an air gap as possible between the coil former which is preferably produced using an injection-molding method often with complex shaping and a rotor which runs in the said coil former is maintained, the invention comprises the special feature that the coil former is formed either by a non-conductive fully ceramic body or is in the form of a composite body in which at least one dimension-stabilizing frame element is embedded by injection molding with plastic in a plastic body which is preferably produced by injection molding.

The invention claimed is:

1. An electric motor comprising a rotor which is surrounded concentrically by a substantially hollow-cylindrical coil former which carries at least one stator winding, the coil former being provided with spoke members, ribs and rib extensions for fixing the at least one stator winding in an exactly structured form, the coil former being in the form of a composite body in which at least one frame element for stabilizing the dimension of the coil former is embedded with plastic in a plastic body by injection molding, wherein the plastic body is produced by injection molding.

2. The electric motor according to claim 1, wherein the frame element comprises a sleeve body.

3. The electric motor according to claim 2, wherein the sleeve body comprises non-conductive material and at least in portions forms a cylindrical inner surface of the coil former.

4. The electric motor according to claim 3, wherein the sleeve body has a wall thickness which is within a range of from (0.01 to 0.03)×D, with D being an inner diameter of the coil former.

5. The electric motor according to claim 4, wherein the wall thickness of the sleeve body is within a range of from 0.1 to 0.5 mm.

6. The electric motor according to claim 1, wherein the frame element is formed by a ceramic component.

7. The electric motor according to claim 6, wherein the ceramic component comprises oxide ceramics.

8. A coil former for an electric motor, the electric motor comprising a rotor which is surrounded concentrically by the coil former, the coil former being a substantially hollow-cylindrical coil former having a composite body in which at least one frame element for stabilizing the dimension of the coil former is embedded with plastic in a plastic body by injection molding, wherein the plastic body is produced by injection molding.

9. The coil former according to claim 8, wherein the coil former has a shape produced by injection molding and having a plurality of fitting surfaces.

10. The coil former according to claim 8, wherein the frame element comprises a sleeve body.

11. The coil former according to claim 10, wherein the sleeve body is made of non-conductive material and at least in portions forms a cylindrical inner surface of the coil former.

12. The coil former according to claim 11, wherein the sleeve body has a wall thickness which is within a range of from (0.01 to 0.03)×D, with D being an inner diameter of the coil former.

13. The coil former according to claim 12, wherein the wall thickness of the sleeve body is within a range of from 0.1 to 0.5 mm.

14. The coil former according to claim 8, wherein the frame element is formed by a ceramic component.

15. An electric motor comprising a rotor which is surrounded concentrically by a substantially hollow-cylindrical coil former which carries at least one stator winding, the coil former being provided with spoke members, ribs and rib extensions for fixing the at least one stator winding in an exactly structured form, the coil former being in the form of a composite body in which at least one frame element for stabilizing the dimension of the coil former is embedded with plastic in a plastic body by injection molding, wherein the plastic body is produced by injection molding, and
wherein the frame element comprises a sleeve body and the sleeve body comprises non-conductive material and at least in portions forms a cylindrical inner surface of the coil former,
wherein the sleeve body has a wall thickness which is within a range of from (0.01 to 0.03)×D, with D being an inner diameter of the coil former.

16. The electric motor according to claim 15, wherein the wall thickness of the sleeve body is within a range of from 0.1 to 0.5 mm.

17. A coil former for an electric motor, the electric motor comprising a rotor which is surrounded concentrically by the coil former, the coil former being a substantially hollow-cylindrical coil former having a composite body in which at least one frame element for stabilizing the dimension of the coil former is embedded with plastic in a plastic body by injection molding, wherein the plastic body is produced by injection molding, and
wherein the frame element comprises a sleeve body and the sleeve body is made of non-conductive material and at least in portions forms a cylindrical inner surface of the coil former,
wherein the sleeve body has a wall thickness which is within a range of from (0.01 to 0.03)×D, with D being an inner diameter of the coil former.

18. The coil former according to claim 17, wherein the wall thickness of the sleeve body is within a range of from 0.1 to 0.5 mm.

* * * * *